United States Patent [19]

Micheli et al.

[11] 4,029,472

[45] June 14, 1977

[54] THERMOELECTRIC EXHAUST GAS SENSOR

[75] Inventors: Adolph L. Micheli; Dennis F. Dungan, both of Mount Clemens, Mich.

[73] Assignee: General Motors Corporation, Detroit, Mich.

[22] Filed: Apr. 5, 1976

[21] Appl. No.: 673,649

[52] U.S. Cl. .......................... 23/254 E; 23/255 E; 60/276; 73/15 B; 136/201; 136/225; 136/236R; 136/239
[51] Int. Cl.² ..................................... G01N 39/02
[58] Field of Search .......... 136/201, 208, 210, 225, 136/239, 236; 73/15 B, 23, 25, 26; 338/28, 32; 123/32 EE; 60/276; 23/232 E, 254 E, 255 E

[56] References Cited

UNITED STATES PATENTS

| | | | |
|---|---|---|---|
| 2,904,995 | 9/1959 | Obermaier | 136/225 |
| 2,994,219 | 8/1961 | Schaschl | 136/225 |
| 3,906,721 | 9/1975 | Micheli et al. | 60/276 |
| 3,913,058 | 10/1975 | Nishio | 338/28 |

Primary Examiner—Harvey E. Behrend
Attorney, Agent, or Firm—Robert J. Wallace

[57] ABSTRACT

An extremely high output and durable thermoelectric sensor for detecting the quantitative content of combustibles in an exhaust gas. Thick film coatings of lithia-nickel and doped titanium dioxide provide two thermocouple junctions on a ceramic substrate. An exhaust gas oxidation catalyst adjacent one of the junctions provides a junction temperature differential when the ceramic body is exposed to exhaust gas flow. The output difference between the two junctions is proportional to the concentration of residual combustibles in the exhaust gas.

5 Claims, 11 Drawing Figures

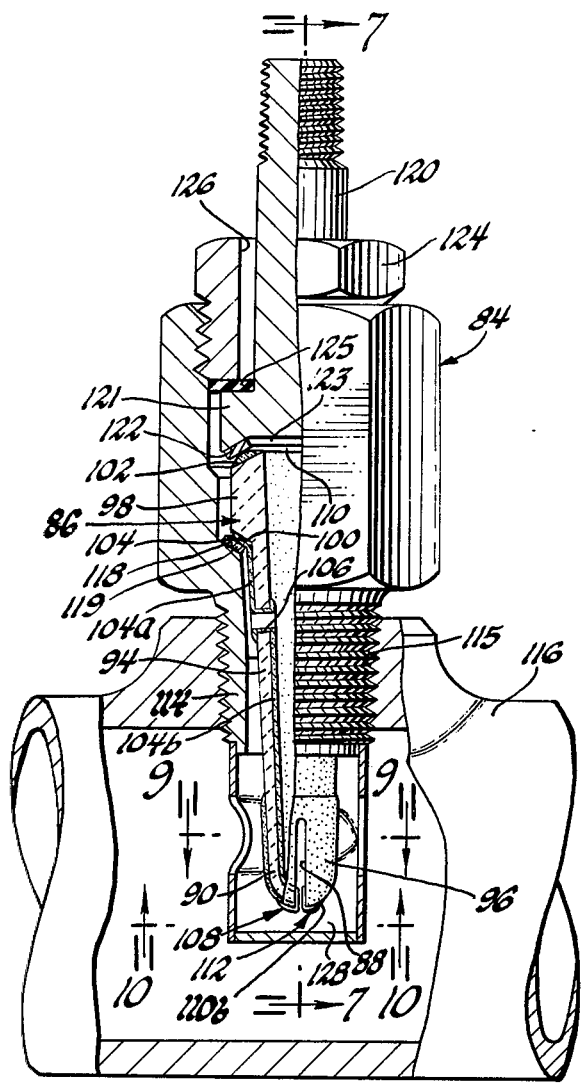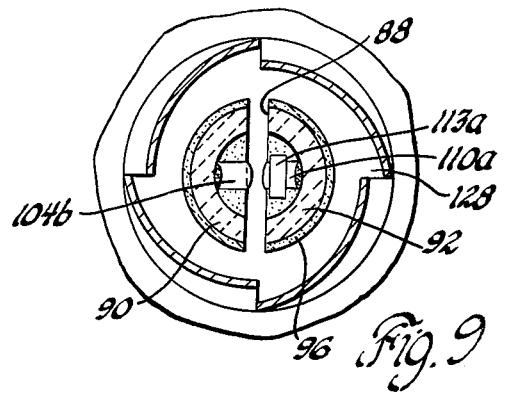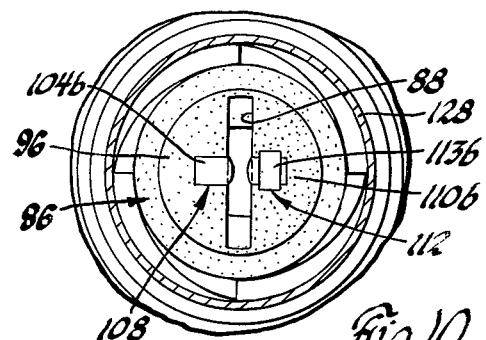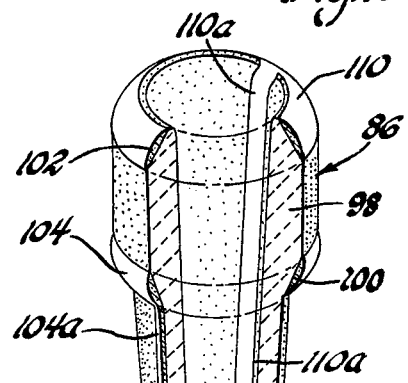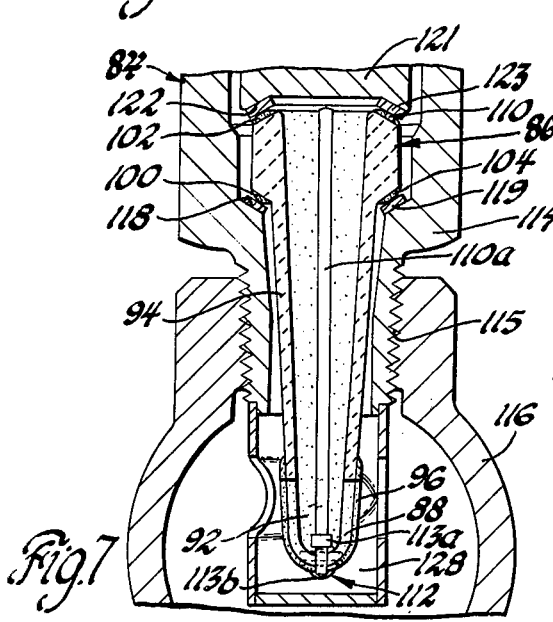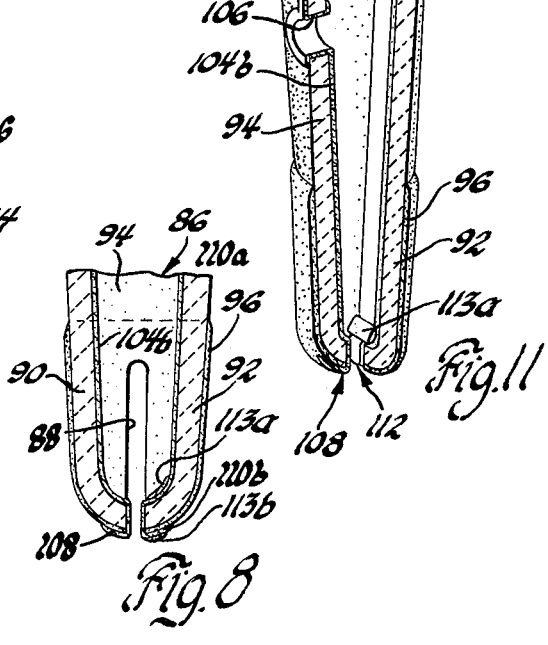

THERMOELECTRIC EXHAUST GAS SENSOR

BACKGROUND OF THE INVENTION

This invention relates to sensors for detecting residual combustibles in exhaust gas, especially internal combustion engine exhaust gas. More particularly, it relates to a thermoelectric device that has a high output, yet which is durable in the highly corrosive and abrasive automobile engine exhaust gas environment.

Thermocouple systems are known for sensing residual combustibles in an exhaust gas. They sense heat generated by oxidizing residual combustibles in an exhaust gas. This heat is proportional, within certain limits, to the concentration of the residual combustibles in the exhaust gas. One junction of a thermocouple can be coated with a catalyst material, while the other junction is left uncoated, to serve as a reference. The residual combustibles oxidize on the catalyst, making the coated junction hotter than the uncoated one. The thermocouple detects the resulting difference in temperature between the two junctions. Such devices can be useful, for example, in monitoring efficiency of an automobile engine and/or its catalytic converter.

Commercially available thermocouple exhaust gas sensors have had their disadvantages. Most devices have not provided an output signal large enough to be easily differentiated from noise that is common to automotive applications. Further, they generally have not been durable in the corrosive and abrasive exhaust gas environment and have been relatively complex to manufacture. Moreover, the design of these sensors introduced inaccuracies in their output. Many also had unwanted thermal gradients between the two thermocouple junctions, caused for example by the decreasing temperature of the exhaust gas as it flows from the engine. Accordingly, such sensors have not been readily accepted in applications which require a reliable, high output device.

U.S. Pat. No. 3,913,058 Micheli et al. discloses a significant improvement in such sensors. Chromel wires forming two separate thermocouple junctions are embedded in the ends of a doped titanium dioxide U-shaped body. An oxidation catalyst in a recess near one of the thermocouple junctions provides the junction temperature differential. This latter device is extremely durable and provides a high output.

We have now found an even higher output device that appears to be as durable. It does not require chromel wires or a large quantity of titanium dioxide. Moreover, our higher output device can be made in a form analogous to a spark plug, facilitating its manufacture in high volume commercial production.

OBJECTS AND SUMMARY OF THE INVENTION

It is, therefore, an object of this invention to provide an improved thermoelectric exhaust gas sensor.

It is a further object of this invention to provide a higher output and durable thermoelectric exhaust gas sensor for an internal combustion engine.

These and other objects of this invention are attained with two separate lithia-nickel thick-film cermet coatings on a ceramic substrate intersecting opposite ends of an elongated doped titanium dioxide thick-film coating on that ceramic substrate. The coatings form two spaced thermocouple junctions. The substrate has a slot between the two junctions. The doped titanium dioxide thick-film coating extends around the slot, so that there is an extended heat flow path from one thermocouple junction to the other. A thick-film oxidation catalyst is adjacent one junction, preferably as a coating over it. The substrate is secured in a housing that is adapted for mounting in an exhaust gas conduit. In a preferred embodiment, the ceramic substate is a hollow cone with a longitudinally extending transverse slot through its apex. A doped titanium dioxide thick-film coating covers the slotted apex and adjoining areas of the cone. Two internal lithia-nickel thick-film strips pass through the slot and intersect the doped titanium dioxide thick-film on opposite halves of the slotted apex. An oxidation catalyst is on the extremity of one half, preferably over the thermocouple junction on that half.

BRIEF DESCRIPTION OF THE DRAWINGS

FIG. 6 is an enlarged fragmentary sectional view in partial elevation showing another embodiment of our exhaust sensor;

FIG. 7 is an enlarged fragmentary view along the line 7—7 of FIG. 6;

FIG. 8 is a further enlarged fragmentary sectional view showing the lower end of the thermoelectric element in the sensor shown in FIG. 6;

FIG. 9 is a sectional view along the line 9—9 of FIG. 6;

FIG. 10 is a sectional view along the line 10—10 of FIG. 6; and

FIG. 11 is a perspective elevational view with parts broken away showing the thermoelectric element in the sensor shown in FIG. 6.

DESCRIPTION OF THE PREFERRED EMBODIMENTS

Figure 1:
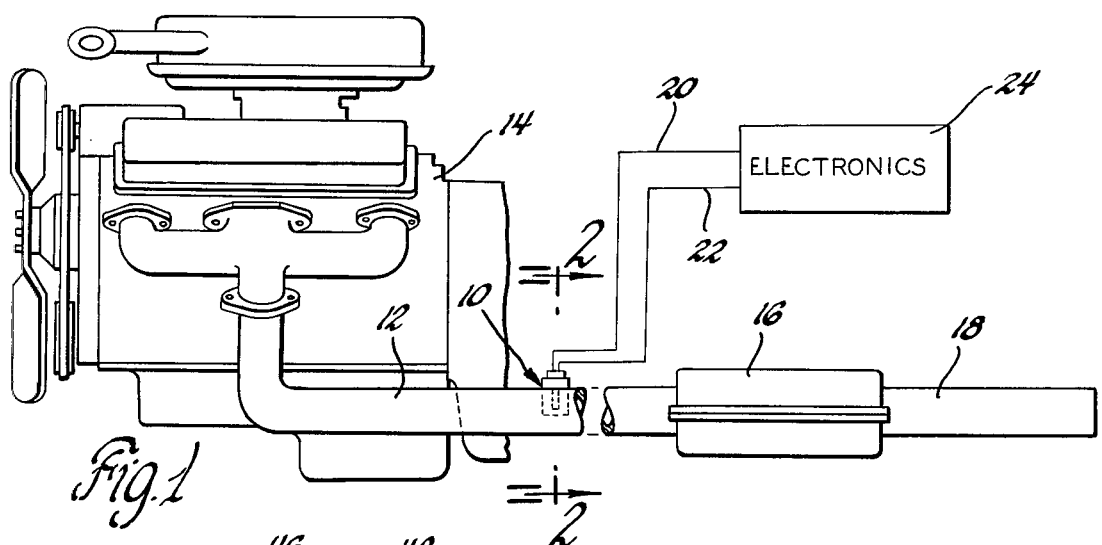
FIG. 1 is a schematic view showing an internal combustion engine and exhaust system having our thermoelectric exhaust gas sensor.
Figure 2:
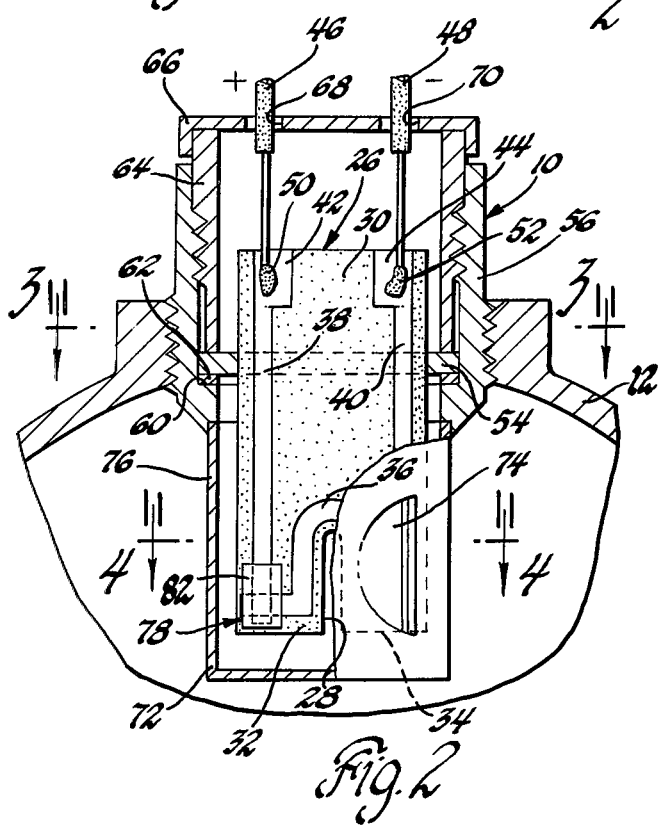
FIG. 2 is an enlarged fragmentary sectional view showing our sensor in partial elevation along the line 2—2 of FIG. 1.
Figure 3:
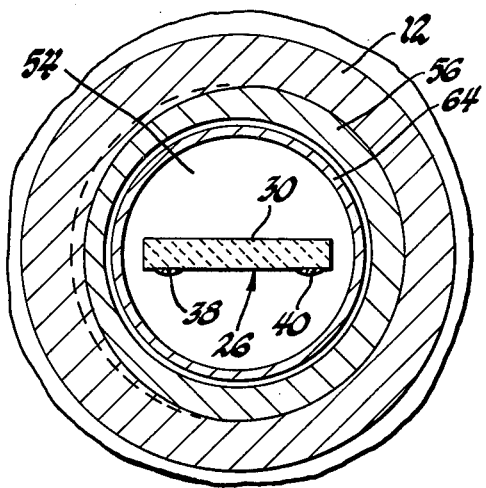
FIG. 3 is a sectional view along the line 3—3 of FIG. 2.
Figure 4:
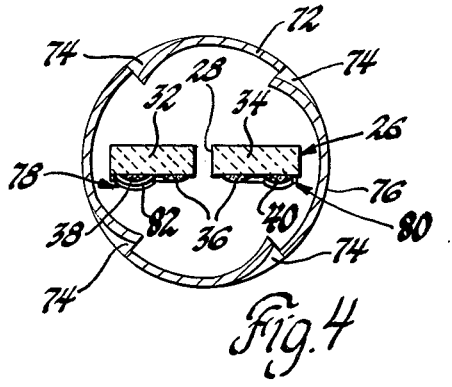
FIG. 4 is a sectional view along the line 4—4 of FIG. 2.
Figure 5:
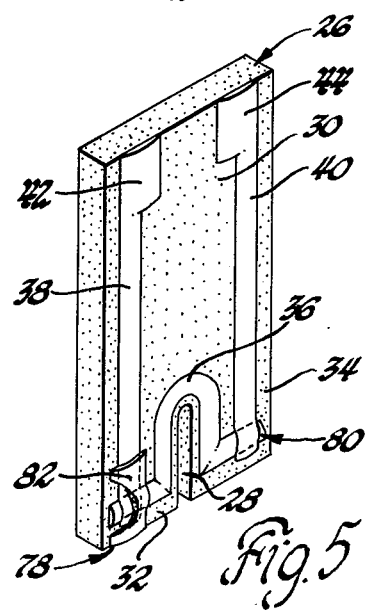
FIG. 5 is a perspective view of the thermoelectric element in the sensor shown in FIG. 2.

FIG. 1 illustrates one of many uses for the exhaust sensor of this invention. The exhaust sensor 10 is mounted in an exhaust pipe 12 that extends from an internal combustion engine 14. Exhaust gases from engine 14 flow through pipe 12 to a catalytic converter 16. Exhaust gases exit the catalytic converter 16 by means of a second exhaust pipe 18, which can be more specifically considered a tailpipe. Sensor 10 is electrically connected by means of leads 20 and 22 to suitable eletronics 24 for monitoring the output of sensor 10. In most instances one of the leads 20 and 22 would be connected to vehicle ground. It may be desirable to ground the sensor to the exhaust pipe through the sensor housing. If so, one of leads 20 and 22 could be physically omitted.

With the sensor 10 disposed upstream from catalytic converter 16, the sensor 10 can detect actual residual amounts of unburned hydrocarbons in the exhaust gas stream. This information can be merely displayed or used for an engine fuel control function, using electronics 24. When the sensor 10 is mounted in exhaust pipe 18 downstream from the catalytic converter, it can be used to monitor efficiency of the catalytic converter.

FIGS. 2 through 5 show a first embodiment of this invention in which the thermoelectric element of this invention is in planar form. The thermoelectric element includes a flat rectangular alumina substrate 26 that is 13 mm wide, 40 mm long, and 2 mm thick. Alumina substrate 26 is oriented to have its length perpendicular and its width transverse to exhaust gas flow. In this instance it is also oriented with its length vertical. Substrate 26 has a slot 28 in its lower end, so that substrate 26 has a body portion 30 and two integral legs 32 and 34. Slot 28 is 10 mm long and 1 mm wide. This is long enough to provide effective thermal separation between the extremities of legs 32 and 34. It should be recognized that the exact leg spacing and length can vary from one embodiment to another depending on a plurality of factors, including the thermal conductivity of the particular ceramic used for substrate 26. However, in most instances we prefer a leg spacing of at least about 0.3 mm.

A continuous thick-film coating 36 of doped titanium dioxide is on the lower end of one face of substrate 26. It is in the form of a strip. The strip extends up from the lower extremity of leg 32, around slot 28 onto substrate body 30, and then down to the lower extremity of leg 34. By the expression "thick-film," we mean a coating of about 0.001 inch or more. Considerably thinner films are likely not to be as durable. Thicker films can be used but for best durability should not be significantly greater than about 0.001 inch. A first lithia-nickel thick-film cermet coating 38 is on the same face of substrate 26 in the form of a vertical strip. The strip extends from an upper portion of substrate body 30 down to the lower extremity of leg 32, where it overlaps the doped titanium dioxide coating 36. A second lithia-nickel thick-film cermet coating 40 on that face of substrate 26 extends from another upper portion of body 30 down to the lower extremity of leg 34, where it overlaps doped titanium dioxide coating 36. The upper ends of the lithia-nickel coatings 38 and 40 have enlarged portions 42 and 44, respectively, to facilitate soldering external leads 46 and 48.

Enlarged portions 42 and 44 may also be separate thick-film coatings of a pure nickel or gold cermet applied to enhance solderability. Leads 46 and 48 are soldered to enlarged portions 42 and 44 at 50 and 52, respectively. The doped titanium dioxide is a material such as disclosed in U.S. Pat. No. 3,913,058 Micheli et al. It is doped with 2 mole percent tantalum pentoxide. However, up to 5 mole percent of any metal from Group V of the Periodic Chart of the Elements can be used. The lithia-nickel cermet contains 10% by weight of a high temperature glass and the balance lithia-nickel in a lithium:nickel molar ratio of 1:9, respectively. On the other hand this ratio can vary from 1:20 to 1:5.

Ceramic substrate 26 extends through a closely conforming aperture in circular alumina plate 54 whose major face is perpendicular to the face of ceramic substrate 26. Substrate 26 is secured to circular plate 54 by a ceramic cermet, or nonconducting glass. The cermet extends completely around the interface between ceramic substrate 26 and circular plate 54 to provide a gas impervious seal.

Ceramic substrate 26 is disposed within a stainless steel tube 56 that has external threads for engagement with internal threads in a circular aperture in an exhaust pipe 12. Tube 56 has an internal circumferential shoulder 60 for supporting circular plate 54. An annular copper or silver sealing ring 62 is disposed between shoulder 60 and circular plate 54. Circular plate 54 is compessed against sealing ring 62 to form a gas tight seal by means of an inner stainless steel tube 64 that is threaded within outer stainless steel tube 56. A cap 66 brazed to the top end of inner stainless steel tube 64 provides external protection for ceramic substrate 26 and the soldered end of leads 46 and 48. Cap 66 has two apertures 68 and 70, through which external leads 46 and 48 extend, respectively.

A stainless steel cup 72, having louvers 74 in its side wall 76, is secured to the lowermost portion of outer tube 56. Cup 72 serves as a shield for the lower end of ceramic substrate 26 to slow down exhaust gas velocity and provide additional protection for ceramic substrate 26 within the exhaust gas environment. Louvered shields for this purpose are more fully described in U.S. Pat. No. 3,844,920 Burgett el al., entitled "Air Fuel Ratio Sensor," which is assigned to the same assignee as this invention.

The thick-film doped titanium dioxide coating 36 is overlapped by the lower end of lithia-nickel thick-film cermet coating 38 at the lower extremity of leg 32 to form a first thermocouple junction 78. The other end of the U-shaped thick-film coating of doped titanium dioxide is overlapped by the lower end of the other lithia-nickel thick-film cermet coating 40, forming a second thermocouple junction 80.

The first thermocouple junction 78 is covered with a thick-film coating 82 of an oxidation catalyst for residual combustibles in the exhaust gas stream in exhaust pipe 12. Preferably the oxidation catalyst is platinum coated gamma alumina particles having a high surface area of about 200 square meters per gram. A more detailed description of such alumina particles may be obtained by reference to U.S. Pat. No. 2,810,699 Voltz et al. It is to be understood that while we prefer this particular oxidation catalyst, other suitable oxidation catalysts can also be used.

In essence, the oxidation catalyst 82 provides a situs for exothermic reaction of residual gas combustibles adjacent one of the two thermocouple junctions 78 and 80. The heat of this exothermic reaction produces a significant temperature increase at thermocouple junction 78. Slot 28 produces an elongated heat flow path in substrate 26 between thermocouple junctions 78 and 80. With most ceramics we prefer a heat flow path at least about 10 mm long. Thus, thermocouple junction 78 is substantially thermally isolated from the exothermic reaction heat at thermocouple junction 80. Accordingly, there is a temperature differential between thermocouple junctions 78 and 80 when they are exposed to an exhaust gas, regardless of the exhaust gas temperature. This temperature differential produces an electrical output between junctions 78 and 80, which can be measured by means of external leads 46 and 48.

The lithia-nickel used in thick-film cermet coatings 38 and 40 has an extremely large positive Seebeck coefficient. For example, the thermocouple response for our thermocouple was measured at 540 microvolts per degree centigrade. This is a significant improvement over the 450 microvolts per degree centigrade reported in U.S. Pat. No. 3,906,721 Micheli et al. for a chromel-doped titanium dioxide thermocouple. Both thermocouples involve equivalent titanium dioxide dopings.

The coatings on the thermocouple element 26 are all produced in the normal and accepted manner for preparing thick-film coatings. They are shown in the drawings in exaggerated thickness for purposes of illustration. The thick-film coatings can be applied by spraying, brushing, or silk screen printing a slurry of the active particles onto the ceramic substrate 26. The slurry ordinarily has a water and/or alcohol vehicle and may contain up to 10% by weight glass as a permanent binder. The doped titanium dioxide and the lithia-nickel cermet coatings are both fired to bond them in place and make them durable in the exhaust gas environment.

The doped titanium dioxide thick-film coating is preferably formed first. The coating material is prepared in a normal and accepted way. For example, a mixture of titanium dioxide and 2 − 5 mole percent tantalum pentoxide is placed in a single stage air fired furnace and heated to 1200° C. This takes about 5 hours. The furnace is held at 1200° C. approximately 1 hour, and heating then discontinued. The furnace is allowed to cool to approximately room temperature which takes about 3 hours. The resultant product is then removed from the furnace and ball milled down to an average particle size of approximately 10 microns or less, using zirconia media and water. After ball milling, the doped titanium dioxide is separated from the zirconia media and dried. It is then placed in a mortar with about 50% by weight (or ml. per 1 gram of doped titanium dioxide) alcohol and/or water, and mixed with a pestle to make a slurry. A small amount, about 0.1% by weight, of an organic deflocculant such as Sea Spin can be mixed into the slurry. We prefer not to include any permanent binder in the slurry. The doped titanium dioxide bonds well to the ceramic substrate all by itself and forms a durable coating that is resistant to deleterious effects of the corrosive exhaust gases. However, it is to be understood that in some instances it may be desirable to include a small amount of a powdered glass in the slurry to enhance bonding and durability. However, in most instances we have found inclusion of such glasses reduces the large negative Seebeck coefficient desirable for this coating.

The slurry is applied to selected areas of the ceramic substrate 26 in the manner previously described for applying a thick-film coating. It is applied as a coating about 0.2 mm thick. The coated substrate is dried for 5 minutes, and then placed in a room temperature single stage controlled atmosphere furnace and heated to a temperature of 1400° C. in a neutral atmosphere or in a vacuum. It is held there for about 10 minutes. Heating to 1400° C. may take about 1 hour. It is then furnace cooled to room temperature in the same atmosphere, taking approximately 2 hours. It should be recognized that application methods, coating thickness and firing temperature are not abnormally critical. They can be varied considerably from the technique herein disclosed.

The lithia-nickel thick-film cermet coatings contain up to 10% of a high temperature glass, with the balance being lithia-nickel in a lithium:nickel molar ratio of 1:9; respectively. While not positively identified, the lithia-nickel is apparently a combination of nickel metal and lithium oxide. As previously mentioned, the lithium:nickel proportions can vary from the preferred 1:9 ratio. Any significant variation from it results in a decrease in the large positive Seebeck coefficient obtained by using the preferred ratio. However, in some instances this can be tolerated, and lithium:nickel molar ratios of 1:20 to 1:5 can be used. The lithia-nickel for the cermet is prepared by heating a mixture containing five mole percent lithium carbonate and 95 mole percent nickel oxide. Lithium carbonate decomposes during heating in air to lithium oxide. If desired, an equivalent amount of lithium oxide can be used directly, or any other material which will produce lithium oxide during heating. Analogously, if desired, equivalent amounts of other nickel compounds can be used if they decompose to nickel oxide when heated in air. The mixture is placed in a room temperature single stage controlled atamosphere furnace and heated to a temperature of 1000° C. in air. It is maintained under this condition for 1 hour, and then furnace cooled to room temperature. Heating to 1000° C. takes about 45 minutes to 1 hour. Furnace cooling takes about 2 hours. The resultant product is a P-type oxide semiconductor. It is then ground down to about 10 microns or less average diameter particle size in a ball mill using zirconia media and water. It is separated from the zirconia media and dried. It is then placed in a mortar along with about one gram per ml. alcohol and/or water and mixed with a pestle to form a slurry. Up to 0.1% by weight of a deflocculant, such as Sea Spin, can be added. In addition, up to 10% by weight of a powdered high temperature glass that can be used in an inert atmosphere is added. Generally at least about 2% is preferred. One such glass that can be used is Owens Illinois type B.

The slurry is then applied to the selected areas of the ceramic substrate 26 by thick-film coating techniques as a 0.2 mm thick coating, and allowed to dry 5 or more minutes. The coated substrate is then placed in a room temperature single stage controlled atmosphere furnace and heated to a selected temperature in a neutral atmosphere, preferably argon. The oxygen partial pressure in the argon atmosphere is maintained very low to obtain the large positive Seebeck coefficient. The maximum amount of oxygen which can be present in the furnace atmosphere varies with furnace temperature. At 1125° C., the oxygen partial pressure should be less than about $1 \times 10^{-8}$ atmospheres. The substrate is heated to 1125° C., held there for about 10 minutes, and then furnace cooled, all while maintaining the special atmosphere. Heat up may take about 45 minutes to 1 hour and cooling about 2 hours.

The substrate should be fired at a temperature of at least 1050° C. in a low oxygen atmosphere to reduce the nickel oxide to free nickel. This forms a lithia-nickel coating having a large positive Seebeck coefficient and makes the lithia-nickel adhere to an alumina substrate. At firing temperatures above about 1250° C., the lithia-nickel tends to bead up on an alumina substrate and provide a discontinuous coating. Accordingly, firing temperatures in excess of about 1250° C. are to be avoided on alumina. The best results on alumina appear to be obtained at a firing temperature of about 1125° C. Equivalent results are expected when firing onto other ceramics at generally similar temperatures.

Analogously, we describe maintaining the substrate at this temperature for about ten minutes when firing the lithia-nickel cermet. However, this particular time can be varied so long as sufficient time is permitted to obtain significant nickel oxide reduction through the entire thickness of the coating. At least about 5 minutes at firing temperature appears to be necessary for coatings of the thickness described herein. Larger times than 10 minutes do not seem to provide any improved results. Correspondingly shorter and longer times may be desirable for thinner and thicker coatings.

The maximum oxygen partial pressure that can be present in the neutral atmosphere and still permit the large positive Seebeck coefficient to be obtained during firing varies with temperature. For example at 1050° C. an oxygen partial pressure no greater than about $1 \times 10^{-10}$ atmosphere can be used. At a firing temperature of about 1250° a maximum partial pressure of about $1 \times 10^{-6}$ atmosphere is permitted. At the preferred firing temperature of 1125° C. the oxygen partial pressure should be no greater than about $1 \times 10^{-8}$ atmosphere.

The oxidation catalyst coating is analogously produced. A slurry of 1 gram gamma alumina per ml. of water and/or alcohol is formed. The gamma alumina has a particle size less than about 10 microns. The slurry also includes a small amount, about 1% by weight, chloroplatinic acid. The slurry is applied to the ceramic substrate 26 over junction 78 by thick-film application techniques. The substrate is dried for at least 5 minutes and then placed in a 500° F. oven for 1 hour in an air atmosphere. After 1 hour it is removed from the oven and placed in open air for cooling to room temperature.

The chloroplatinic acid need not be included in the slurry. It can be added by wetting the gamma alumina thick-film coating 82 with an aqueous solution of it immediately prior to placement in the oven. While we prefer to use the platinum coated gamma alumina as an oxidation catalyst, it is to be understood that other oxidation catalysts durable under the exhaust gas environment could also be used. Also, we prefer to apply the catalyst as a coating directly over the junction for maximum heating effect. However, it should be recognized that this coating can be applied around the junction, on the opposite surface of leg 22, and/or in openings in the ceramic of leg 22 near the junction.

Reference is now made to FIGS. 6 – 11 which show an alternate embodiment of our sensor. The sensor 84 contains a thermoelectric element 86 having thick-film coatings on it formed in a manner identical to that described in connection with the preceding embodiment of the invention. The thermoelectric element 86 in sensor 84 is a hollow, generally conical alumina body having an apex which is slightly rounded. Cone 86 is about 35 mm long and has an inner diameter of about 5 mm at its top end. Its apex has a radius of curvature of about 2 mm, making the apex more rugged. Wall thickness of cone 86 is generally about 1 mm, except at its top end. An axially extending transverse slot 88 divides the apex of cone 86 into two legs 90 and 92. Legs 90 and 92 are thus integrally connected to the remaining body portion 94 of cone 86. Slot 88 is 0.5 mm wide and 15 mm long. A doped titanium dioxide thick-film coating 96 completely covers legs 90 and 92 as well as an adjoining part of body portion 94 above slot 88. Accordingly, there is a continuous current flow path in this coating from one leg to the other around slot 88 through the doped titanium dioxide coating.

A circumferential cylindrical outer enlargement 98 about 14 mm in diameter is on the top end of cone 86. It interrupts the conical outer surface of cone 86 and provides a lower circumferential external tapered shoulder 100 and an upper circumferential external tapered shoulder 102. Shoulders 100 and 102 are about 3 mm wide. The taper is with respect to the axis of cone 86. While not preferred, shoulders 100 and 102 can be perpendicular to the axis of cone 86. A circumferential lithia-nickel thick-film cermet coating 104 on shoulder 100 has a strip 104a extending down therefrom on the outer surface of cone 86. Strip 104a extends down to an aperture 106 in cone 86, and passes through the aperture to intersect with lithia-nickel thick-film strip 104b on the inner surface of the cone. Strip 104b continues on from aperture 106 down to the bottom of leg 90, and then, passing through slot 88, it continues out onto doped titanium dioxide coating 96. The lower end of strip 104b thus overlaps the doped titanium dioxide coating 96 on the outer surface of leg 90, forming a first thermocouple junction 108. A second lithia-nickel thick-film cermet coating 110 covers shoulder 102 and has an extension 110a extending down the inner surface of cone 86 to leg portion 92. The lower end 110b of extension 110a passes through slot 88 onto the outer surface of the doped titanium dioxide coating covering leg 92, forming a second thermocouple junction 112. The lower extremity of leg 92 has a thick-film coating 113a and 113b of platinum coated gamma alumina on both its inner and outer surface, respectively. Coating 113b preferably is over thermocouple junction 112, as shown. The additional inner coating 113a insures junction 112 will be at maximum temperature difference.

Cone 86 is disposed within a stainless steel tube 114 that is externally threaded at its lower end for seating within a threaded circular aperture 115 of an exhaust pipe 116. Tube 112 has an internal circumferential tapered shoulder 118 on which a frusto-conical copper sealing ring 119 is disposed. Ring 119 provides a hermetic seal between tube shoulder 118 and cone lower shoulder 100. Above cone 86 is a stainless steel solid rod 120 that has an enlarged circular lower end 121. Lower end 121 has a tapered circumferential shoulder 122 on its lower surface for coaction with coated cone shoulder 102 through a frusto-conical copper hermetic sealing ring 123.

A louvered stainless steel cup 128 is secured to the lower end of tube 114. It is similar to cup 72 in the preceding example of the invention and serves the same purpose.

An externally threaded clamp nut 124, engaging internal threads on the upper end of tube 114, applies mechanical force to rod lower end 121 through a mica washer 125. Clamp nut 124 has an axial aperture 126 of greater diameter than that of rod 120 and is coaxial with rod 120. Hence, the two are radially spaced from one another and radially electrically isolated. Mica washer 125 completes electrical insulation of clamp nut 124 from rod 120. Threads on the upper end of rod 120 permit quick attachment of an electrical lead (not shown) to the sensor, for electrical communication with lithia-nickel thick-film cermet coating 110. No separate second electrical terminal is necessary in this embodiment of the invention. Circumferential lithia-nickel thick-film coating 104 electrically communicates with outer stainless steel tube 114 through the copper sealing washer 119. Tube 114 is in electrical communication with, grounded to, exhaust pipe 116.

We claim:

1. In an internal combustion engine exhaust system having a conduit for directing a stream of exhaust gases, a durable and high output thermoelectric exhaust gas sensor in said conduit for detecting residual combustibles in said exhaust gas stream, said sensor comprising:

an electrically nonconductive ceramic element having a body portion and two integral mutually spaced legs, said legs serving as a support for at least two interconnected high output thermocouple junctions;

a continuous coating of doped titanium dioxide on said element extending from an extremity of one leg to an extremity of the other leg via said body portion, said titanium dioxide coating containing a dopant that is a pentavalent ion from Group V of the Periodic Table of the Elements and having a large negative Seebeck coefficient;

a first continuous coating of lithia-nickel on said element extending from said body portion to one leg extremity where it contacts said doped titanium dioxide coating, said lithia-nickel coating having a large positive Seebeck coefficient and forming a first high output thermocouple junction with said doped titanium dioxide coating at said one leg extremity that is resistant to corrosive and abrasive effects of an internal combustion engine exhaust gas stream;

a second continuous coating of lithia-nickel on said element extending from said body portion to the other leg extremity where it contacts said doped titanium dioxide coating, said second lithia-nickel coating having a large positive Seebeck coefficient similar to said first lithia-nickel coating and forming a second high output thermocouple junction with said doped titanium dioxide coating at said other leg extremity that is resistant to corrosive and abrasive effects of an internal combustion engine exhaust gas stream;

a coating of catalytic ceramic particles on only one of said leg extremities closely adjacent the one thermocouple junction thereon and providing a high surface area situs for exothermic reaction of residual combustibles in an internal combustion engine exhaust gas stream;

means attached to said body portion for mounting said element in an exhaust system conduit and uniformly exposing both leg extremities, including said first and second thermocouple junctions, to the exhaust gas stream whereby residual exhaust gas combustibles can react with said catalytic ceramic particles adjacent the one thermocouple junction and produce a temperature differential between it and the other thermocouple junction;

means on said body portion, spaced from said doped titanium dioxide coating, for making separate electrical connections to said first and second lithia-nickel coatings; and means for isolating said electrical connections from exhaust gas in said exhaust system conduit so that said electrical connections are not deleteriously affected while said thermocouple junctions are exposed to said exhaust gas stream.

2. A durable and high output thermoelectric exhaust gas sensor for detecting the quantitative content of residual combustibles in an internal combustion engine exhaust gas stream, said sensor comprising:

an electrically nonconductive ceramic element having an end serving as a support for at least two interconnected high output thermocouple junctions;

a slot in said element end forming two mutually spaced legs integrally connected to a body portion of said element;

a first continuous thick-film coating of lithia-nickel on said element extending from an extremity of one leg to a first region of said body portion significantly spaced from said slot, said lithia-nickel coating having a large positive Seebeck coefficient;

a second continuous coating of lithia-nickel on said element extending from an extremity of the other leg to a second region of said body portion significantly spaced from said slot, said second lithia-nickel coating having a large positive Seebeck coefficient similar to said first lithia-nickel coating;

a continuous thick-film coating of doped titanium dioxide on said element extending from said one leg extremity to said other leg extremity around said slot via said body portion, said titanium dioxide coating containing a dopant that is a pentavalent ion from Group V of the Periodic Table of the Elements and having a large negative Seebeck coefficient;

an overlapping contact between said doped titanium dioxide coating and each of said first and second lithia-nickel coatings at said one and other leg extremities forming first and second spaced high output thermocouple junctions that are resistant to corrosive and abrasive effects of an internal combustion engine exhaust gas stream;

a coating of catalytic ceramic particles on only one of said thermocouple junctions providing a high surface area situs for exothermic reaction of residual combustibles in said exhaust gas stream that produces a temperature differential between said first and second thermocouple junctions when exposed to an internal combustion engine exhaust stream;

means for mounting said element in an internal combustion engine exhaust system conduit and exposing both leg extremities, including said first and second thermocouple junctions, to the exhaust gas stream;

means for making separate electrical connections in said first and second regions to said first and second lithia-nickel coatings; and means for isolating said electrical connections from exhaust gas in said exhaust system conduit so that said electrical connections are not deleteriously affected while said thermocouple junctions are exposed to said exhaust gas stream.

3. A durable and high output thermoelectric sensor for detecting residual combustibles in an internal combustion engine exhaust gas system, said sensor comprising:

a plate-like electrically nonconductive ceramic element having a body portion and one end providing a face for supporting two high output thermocouple junctions;

a slot in said one element end dividing said one element end into two mutually spaced legs;

a continuous thick-film coating of doped titanium dioxide on said face extending from an extremity of one leg to an extremity of the other leg via said body portion, said doped titanium dioxide coating containing a dopant that is a pentavalent ion from Group V of the Periodic Table of the Elements and having a large negative Seebeck coefficient;

a first continuous thick-film coating of lithia-nickel on said face extending from a first region of said body portion into overlapping relationship with said doped titanium dioxide coating at one leg extremity, said lithia-nickel coating having a large positive Seebeck coefficient and forming a first high output thermocouple junction with said doped titanium dioxide coating at said one leg portion extremity that is resistant to corrosive and abrasive effects of an internal combustion engine exhaust gas stream;

a second continuous thick-film coating of lithia-nickel on said face extending from a second region of said body portion into overlapping relationship with said doped titanium dioxide coating at the other leg extremity, said second lithia-nickel coating having a large positive Seebeck coefficient similar to said first lithia-nickel coating and forming a second high output thermocouple junction with said doped titanium dioxide coating at said other leg extremity that is resistant to corrosive and abrasive effects of the internal combustion engine exhaust gas stream;

a coating of catalytic ceramic particles on said face over only one of said thermocouple junctions and providing a high surface area situs closely adjacent said one thermocouple junction for exothermic reaction of residual combustibles in an exhaust gas stream;

means attached to said body portion for mounting said element in an exhaust system conduit and uniformly exposing both leg extremities, including said first and second thermocouple junctions, to the exhaust gas stream whereby residual combustibles in the exhaust gas can react with said catalytic ceramic particles and produce a temperature differential between said first and second thermocouple junctions;

means on said body portion spaced from said doped titanium dioxide coating for making separate electrical connections and to said first and second lithia-nickel thick-film coatings near an opposite end on said body portion; and means for isolating said electrical connections from exhaust gas in said exhaust system conduit so that said electrical connections are not deleteriously affected while said thermocouple junctions are exposed to said exhaust gas stream.

4. In an internal combustion engine exhaust system having a pipe for directing a stream of exhaust gas, a durable high output thermoelectric exhaust gas sensor in said pipe for detecting the quantitative content of exhaust gas residual combustibles, said sensor comprising:

a hollow, generally conical electrically nonconductive ceramic element having an apex serving as a support for at least two interconnected high output thermocouple junctions;

an axially extending transverse slot in said element apex, dividing said apex into two mutually spaced generally frusto-conical legs integral with a generally conical body portion;

inner and outer surfaces on said generally conical element in communication with one another through said apex slot;

a continuous thick-film coating of doped titanium dioxide on said element outer surface extending from an extremity of one leg to an extremity of the other leg via said body portion, said titanium dioxide coating containing a dopant that is a pentavalent ion from Group V of the Periodic Table of the Elements and having a large negative Seebeck coefficient;

a first continuous thick-film coating of lithia-nickel on said element inner surface extending from a first region of said body portion to one leg extremity through said slot and out onto the outer surface of said leg extremity where it contacts said doped titanium dioxide coating in an overlapping relationship, said lithia-nickel coating having a large positive Seebeck coefficient and forming a first high output thermocouple junction with said doped titanium dioxide coating at said one leg portion extremity that is resistant to corrosive and abrasive effects of the internal combustion engine exhaust gas stream;

a second continuous thick-film coating of lithia-nickel on said element inner surface extending from a second region of said body portion to the other leg extremity through said slot and out onto the outer surface of said leg extremity where it contacts said doped titanium dioxide coating in an overlapping relationship, said second lithia-nickel coating having a large positive Seebeck coefficient similar to said first lithia-nickel coating and forming a second high output thermocouple junction with said doped titanium dioxide coating at said other leg extremity that is resistant to corrosive and abrasive effects of the internal combustion engine exhaust gas stream;

a coating of catalytic ceramic particles on at least the outer surface of only one of said legs over the thermocouple junction thereon and providing a high surface area situs closely adjacent said one thermocouple junction for exothermic reaction of residual combustibles in an exhaust gas stream;

a generally cylindrical and coaxial enlargement on said element body portion axially spaced away from said slot and providing apex-facing and opposite-facing circumferential shoulders on the outer surface of said element body portion;

an aperture in said body portion communicating said inner and outer surfaces of said element in a region between said apex-facing shoulder and said slot;

an extension of said first lithia-nickel thick-film coating passing through said aperture from said inner surface out onto said outer surface and further extending to and circumferentially around said apex-facing shoulder;

an extension of said second lithia-nickel thick-film coating extending to and circumferentially around said opposite-facing shoulder;

first means for concurrently electrically contacting said first lithia-nickel thick-film coating on said apex-facing shoulder and circumferentially sealing said apex-facing shoulder with respect to internal combustion engine exhaust gas;

second means for concurrently electrically contacting said second lithia-nickel thick-film coating on said opposite-facing shoulder and for biasing said opposite-facing shoulder towards said apex, in cooperation with said first means, to maintain said apex-facing shoulder in sealing relationship with said first means;

insulating means for maintaining said first and second contact means electrically isolated from one another; and external circumferential threads on said first contact means for mounting said element in an internally threaded aperture in an internal combustion engine exhaust conduit, whereby both of said thermocouple junctions can be uniformly exposed to an exhaust gas stream to establish a potential difference between said first and second electrical contact means and said aperture is substantially sealed.

5. A method of making a durable and high output thermoelectric sensor for detecting the quantitative content of residual combustibles in exhaust gas from an internal combustion engine, said method comprising the steps of:

providing a ceramic substrate having a slot at one end that forms two mutually spaced legs that are integral with an element body portion;

applying to said substrate a thick-film coating of doped titanium dioxide that extends in a continuous pattern from the extremity of one leg to the extremity of the other leg via said body portion, said titanium dioxide coating containing a dopant that is a pentavalent ion from Group V of the Periodic Table of the Elements;

heating said substrate to obtain an adherent coating having a large negative Seebeck coefficient;

applying to said substrate a first thick-film coating of lithia-nickel oxide in a molar ratio of about 1:9 in a pattern that overlaps the doped titanium dioxide coating at one leg extremity and extends to a first region of said body portion spaced from said slot;

applying to said substrate a second thick-film coating of lithia-nickel oxide in a molar ratio of about 1:9 in a pattern that overlaps said doped titanium dioxide coating at one leg extremity and extends to a second region of said body portion spaced from said slot;

heating said coated element to a temperature of approximately 1050°–1250° C. in a low oxygen atmosphere for a sufficient duration to reduce said nickel oxide and produce a large positive Seebeck coefficient in said first and second lthia-containing thick-film coatings, said atmosphere having a maximum oxygen partial pressure of about $1 \times 10^{-10}$ atmosphere at 1050° C. and $1 \times 10^{-6}$ atmosphere at 1250° C., whereby each of said first and second thick-film coatings becomes lithia-nickel thick-film coating bonded to said substrate and each forms a durable, high output thermocouple junction where it overlaps said doped titanium dioxide thick-film coating;

applying to only one of said thermocouple junctions a thick-film coating of a catalytic material which will provide a high surface area situs for exothermic reaction of residual combustibles in said exhaust gas; and assembling said element into means for mounting said element in an exhaust system conduit so that exhaust gas therein can react on said catalytic material and produce an electrical potential difference between said thermocouple junctions.

* * * * *